(12) United States Patent
Lampropoulos et al.

(10) Patent No.: US 8,123,763 B2
(45) Date of Patent: Feb. 28, 2012

(54) SUTURE SECUREMENT APPARATUS

(75) Inventors: Fred P. Lampropoulos, Salt Lake City, UT (US); Timothy W. Clark, Philadelphia, PA (US); Gregory McArthur, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 924 days.

(21) Appl. No.: 12/106,204

(22) Filed: Apr. 18, 2008

(65) Prior Publication Data

US 2008/0269785 A1 Oct. 30, 2008

Related U.S. Application Data

(63) Continuation-in-part of application No. 11/244,168, filed on Oct. 6, 2005, now abandoned.

(60) Provisional application No. 61/036,903, filed on Mar. 14, 2008.

(51) Int. Cl.
A61B 17/04 (2006.01)
(52) U.S. Cl. ....................................................... 606/144
(58) Field of Classification Search .................. 606/139, 606/144, 148, 228, 113
See application file for complete search history.

(56) References Cited

U.S. PATENT DOCUMENTS

| | | | |
|---|---|---|---|
| 3,452,740 A | 7/1969 | Muller | |
| 4,796,626 A * | 1/1989 | DeVries | 606/148 |
| 4,799,496 A | 1/1989 | Hargreaves et al. | |
| 4,829,999 A | 5/1989 | Auth | |
| 4,858,810 A | 8/1989 | Intlekofer et al. | |
| 4,860,742 A | 8/1989 | Park et al. | |
| 4,957,117 A | 9/1990 | Wysham | |
| 4,973,329 A | 11/1990 | Park et al. | |
| 5,137,517 A | 8/1992 | Loney et al. | |
| 5,161,534 A | 11/1992 | Berthiaume | |
| 5,219,332 A | 6/1993 | Nelson et al. | |
| 5,312,338 A | 5/1994 | Nelson et al. | |
| 5,325,746 A | 7/1994 | Anderson | |

(Continued)

FOREIGN PATENT DOCUMENTS

EP 534747 3/1993

(Continued)

OTHER PUBLICATIONS

Notification of Transmittal of the International Search Report and the Written Opinion of the International Searching Authority issued Dec. 14, 2007 in International Application No. PCT/US2007/06945.

(Continued)

*Primary Examiner* — Melanie Tyson
*Assistant Examiner* — Son Dang
(74) *Attorney, Agent, or Firm* — Stoel Rives LLP

(57) ABSTRACT

A suture securement apparatus for selectively securing one or more ends of a suture while allowing adjustments in the tension or a full release of the sutures intermittently after a prolonged period of time. The suture securement apparatus can be particularly adapted for use with a purse-string suture to close a percutaneous catheter puncture site without causing puckering or distortion of the skin at the purse string suture site. The suture securement apparatus permits a practitioner to subsequently modify the amount of tensioning or full release of the sutures at the catheter insertion site. A threading assembly for use with the suture securement apparatus and being adapted to facilitate threading of sutures along the length of the suture securement apparatus.

9 Claims, 4 Drawing Sheets

U.S. PATENT DOCUMENTS

| | | | |
|---|---|---|---|
| 5,325,868 A * | 7/1994 | Kimmelstiel | 600/585 |
| 5,392,778 A | 2/1995 | Horzewski | |
| 5,423,331 A | 6/1995 | Wysham | |
| 5,634,475 A | 6/1997 | Wolvek | |
| 5,741,301 A | 4/1998 | Pagedas | |
| 5,800,447 A | 9/1998 | Wenstrom, Jr. | |
| 5,851,189 A | 12/1998 | Forber | |
| 5,919,161 A | 7/1999 | Hill, III et al. | |
| 5,971,994 A * | 10/1999 | Fritzsch | 606/113 |
| 5,987,344 A | 11/1999 | West | |
| 6,015,428 A | 1/2000 | Pagedas | |
| 6,030,349 A | 2/2000 | Wilson et al. | |
| 6,033,414 A | 3/2000 | Tockman et al. | |
| 6,059,484 A | 5/2000 | Greive | |
| 6,171,317 B1 | 1/2001 | Jackson et al. | |
| 6,371,940 B1 | 4/2002 | Valencia et al. | |
| 6,394,976 B1 | 5/2002 | Winston et al. | |
| 6,533,772 B1 | 3/2003 | Sherts et al. | |
| 6,626,917 B1 | 9/2003 | Craig | |
| 6,949,104 B2 | 9/2005 | Griffis et al. | |
| 7,011,635 B1 | 3/2006 | Delay | |
| 7,087,060 B2 | 8/2006 | Clark | |
| 7,144,378 B2 | 12/2006 | Arnott | |
| 2001/0031973 A1 | 10/2001 | Nobles et al. | |
| 2002/0026202 A1 * | 2/2002 | Honey et al. | 606/127 |
| 2003/0028203 A1 | 2/2003 | Clark | |
| 2003/0225395 A1 | 12/2003 | Griffis et al. | |
| 2003/0229297 A1 | 12/2003 | Christensen et al. | |
| 2004/0067099 A1 | 4/2004 | Warburton-Pitt | |
| 2004/0215108 A1 | 10/2004 | Windheuser | |
| 2005/0070820 A1 | 3/2005 | Boutillette et al. | |
| 2005/0096566 A1 | 5/2005 | Arnott | |
| 2005/0235778 A1 | 10/2005 | Murphy et al. | |
| 2006/0030886 A1 | 2/2006 | Clark | |
| 2007/0142786 A1 | 6/2007 | Lampropoulos et al. | |
| 2007/0219467 A1 | 9/2007 | Clark et al. | |
| 2008/0269785 A1 | 10/2008 | Lampropoulos et al. | |

FOREIGN PATENT DOCUMENTS

WO     WO 01/41860     6/2001

OTHER PUBLICATIONS

Notification of Transmittal of the International Search Report and the Written Opinion of the International Searching Authority issued Jun. 25, 2009 in International Application No. PCT/US2009/037168.
European Search Report issued May 29, 2009 in co-pending European patent application No. 07753564.9.
Vorwerk, Konner, Schurmann, and Gunther, a Simple Trick to Facilitate Bleeding Control after Percutaneous Hemodialysis Fistula and Graft Interventions, Cardiovasc Intervent Radiol 20 (2) : 159-60 (1997).
Zaleski, Funaki, Gentile, and Garofalo, Purse-string Sutures and Miniature Tourniquet to Achieve Immediate Hemostasis of Percutaneous Grafts and Fistulas: a Simple Trick with a Twist, Am. J. Roentgenol. 175 (6) : 1643-5 (2000).
Simmons, Clark, and Rajan, The Woggle Technique: A New Method of Suture Closure of Hemodialysis Arteriovenous Grafts and Fistulae After Percutaneous Intervention, Journal of Vascular and Interventional Radiology 12(1) :S30 (2001).
Notice of Allowance issued Jan. 10, 2006 in co-pending U.S. Appl. No. 10/198,161.
Response and Amendment filed Oct. 6, 2005 in co-pending U.S. Appl. No. 10/198,161.
Office Action issued Apr. 6, 2005 in co-pending U.S. Appl. No. 10/198,161.
Office Action issued Feb. 7, 2005 in co-pending U.S. Appl. No. 10/198,161.
Preliminary Amendment filed Oct. 6, 2005 in co-pending U.S. Appl. No. 11/244,168.
Office Action issued Feb. 6, 2007 in co-pending U.S. Appl. No. 11/244,168.
Amendment filed Aug. 6, 2007 in co-pending U.S. Appl. No. 11/244,168.
Examiner Interview Summary in co-pending U.S. Appl. No. 11/244,168.
Office Action issued Oct. 18, 2007 in co-pending U.S. Appl. No. 11/244,168.
Notice of Abandonment issued Aug. 7, 2008 in co-pending U.S. Appl. No. 11/244,168.
Office action dated Mar. 16, 2010 in U.S. Application No. 11/688,766.
Notice of allowance dated Jan. 10, 2006 in U.S. Application No. 10/198,161.
Office action dated Apr. 6, 2005 in U.S. Application No. 10/198,161.
Office action dated Feb. 7, 2005 in U.S. Application No. 10/198,161.
Office action dated Feb. 6, 2007 in U.S. Application No. 11/244,168.
Office action dated Oct. 18, 2007 in U.S. Application No. 11/244,168.
Notice of abandonment dated Aug. 7, 2008 in U.S. Application No. 11/244,168.
Office action dated Jun. 11, 2010 in U.S. Application No. 11/688,766.
Office Action dated Oct. 21, 2011 in U.S. Appl. No. 12/404,227.
Office Action dated Oct. 24, 2011 in U.S. Appl. No. 12/202,073.

* cited by examiner

SUTURE SECUREMENT APPARATUS

CROSS REFERENCE TO RELATED APPLICATIONS

This application claims the benefit of U.S. Provisional Patent Application No. 61/036,903, filed on Mar. 14, 2008, the entire contents of which are herein incorporated by reference and claims the benefit of and is a continuation-in-part of pending U.S. patent application Ser. No. 11/244,168, filed on Oct. 6, 2005 in the name of Dr. Timothy W. Clark, which claims the benefit of U.S. Provisional Patent Application No. 60/307,042, filed on Jul. 20, 2001, the entire contents of which are herein incorporated by reference.

BACKGROUND OF THE INVENTION

1. Field of the Invention

The present invention relates to a suture securement apparatus. In more particular, the present relates to a suture securement apparatus which is utilized in connection with a threading assembly to provide desired securement of percutaneous catheter puncture wounds and/or drainage catheter apparatus.

2. Relevant Technology

One of the challenges that is often encountered in the use of percutaneous catheter insertion relates to the maintaining of the catheter within the catheter insertion site and also the proper maintenance of homeostasis subsequent to removal of the catheter from the catheter insertion site. A variety of different suturing techniques have been utilized in connection with percutaneous catheter puncture wounds and the maintenance of catheters within the percutaneous catheter insertion sites. However, inadvertent slipping or removal of catheters and desired closure of percutaneous catheter puncture wounds subsequent to removal of such catheters has resulted in undesirable patient discomfort and at times a partial or total loss of homeostasis.

One of the techniques that is often utilized with percutaneous catheter puncture wounds is the use of a purse string suture. A purse string suture is formed by inserting a suture, such as a monofilament or braided thread into the patient's skin at a position adjacent the puncture site. The practitioner then forms a circular series of continuous stitches which parallel the edges of the wound in a substantially circular pattern. The configuration of the stitches results in a plurality of segments of suture which alternate between being threaded under a portion of the patient's skin and being position over the surface of the patient's skin. Typically, the resulting suture configuration has between three and four segments of stitches which are positioned above the skin around the edges of the wound. A tail of the suture extends from both the pre-insertion site and also at the emergent site such that the purse string suture appears to have two tails which emerge somewhat close in proximity to one another at a predetermined point around the edge of the puncture wound.

The purse string sutures allow a practitioner to close the wound by simply pulling on the two ends of the suture thus tightening the suture which is then threaded around the perimeter of the wound site. Pulling the tails of the purse string sutures effectively closes the wound site and results in the desired homeostasis. In this manner, excessive compression or other techniques which are typically utilized to stop puncture wound bleeding are not needed.

One of the challenges which has been experienced with purse string suture closure methods and the desired maintaining of homeostasis utilizing the purse string suture relates to the knotting or other techniques for maintaining tension on the adjacent ends of the purse string suture. One mechanism which has been utilized employs a knot at one end of one suture which engages the other suture to maintain the desired tension of the overall length of the purse string suture. However, the knot utilized in connection with such techniques can compromise the integrity of the purse string suture. Additionally, the knot can make subsequent loosening and retightening of the purse string suture difficult if not impossible. Additionally, non-doctor practitioners may be unwilling or uncomfortable with removing such sutures at the end of the procedure. As a result, the doctor must see the patient to remove the suture, or the patient may be required to come in for an office visit that may be inconvenient or otherwise impractical.

Another technique which has been utilized is to attempt to utilize a secondary securement apparatus to secure the ends of the suture. However, such techniques often result in excessive tension on the purse string suture which can cause puckering or unnatural distortion of the patient's skin adjacent the purse string suture site. As a result, unnecessary discomfort and/or damage to the patient tissue can result.

BRIEF SUMMARY OF THE INVENTION

Figure 1:
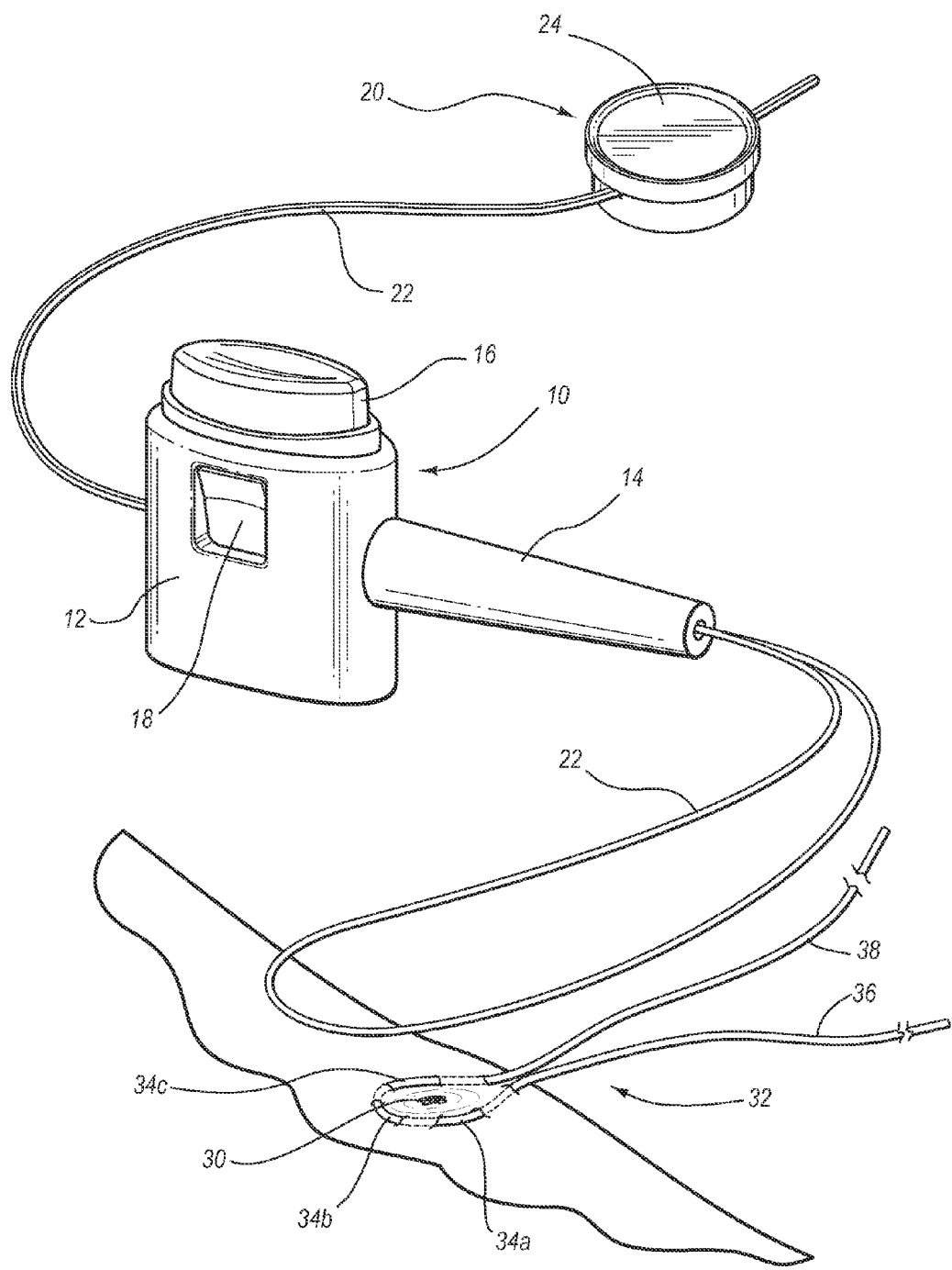
FIG. 1 is a perspective view of a suture securement apparatus utilized in connection with a threading assembly for maintaining hemostasis at a puncture site according to one embodiment of the present invention.

The present invention relates to a suture securement apparatus for selectively securing one or more ends of a suture while allowing adjustments in the tension or a full release of the sutures intermittently after a prolonged period of time. The suture securement apparatus can be particularly adapted for use with a purse-string suture to close a percutaneous catheter puncture site without causing puckering or distortion of the skin at the purse string suture site. The suture securement apparatus permits a practitioner to subsequently modify the amount of tensioning or full release of the sutures at the catheter insertion site. The present invention also relates to a threading assembly for use with the suture securement apparatus which is adapted to facilitate threading of sutures along the length of the suture securement apparatus.

According to one embodiment of the present invention the suture securement apparatus includes an extension tube for facilitating tensioning of the sutures at the suture insertion site. The length and shape of the extension tube also permits positioning of the tip of the extension tube adjacent the suture insertion site. According to another embodiment of the present invention, a threading assembly is provided in connection with the suture securement assembly. The threading assembly allows a practitioner to quickly and simply thread one or more tails of the suture from the exterior of the suture securement apparatus and through a lumen of the suture securement apparatus such that desired engagement of such sutures is facilitated.

According to one embodiment of the present invention, a clasp and suture loop are provided as part of the threading assembly. The clasp prevents the accidental pulling of the suture loop through the suture securement apparatus as a result of the tension exerted on the portion of the suture loop positioned distal to the suture securement apparatus. Additionally, the clasp provides a simple and ergonomical mechanism to allow a user to control functioning of the threading assembly and of the suture securement loop.

DETAILED DESCRIPTION

The present invention relates to a suture securement apparatus for selectively securing one or more ends of a suture while allowing adjustments in the tension or a full release of the sutures intermittently after a prolonged period of time. The suture securement apparatus can be particularly adapted for use with a purse-string suture to close a percutaneous catheter puncture site without causing puckering or distortion of the skin at the purse string suture site. The suture securement apparatus permits a practitioner to subsequently modify the amount of tensioning or full release of the sutures at the catheter insertion site. The present invention also relates to a threading assembly for use with the suture securement apparatus and being adapted to facilitate threading of sutures along the length of the suture securement apparatus.

According to one embodiment of the present invention the suture securement apparatus includes an extension tube for facilitating tensioning of the sutures at the suture insertion site. The length and shape of the extension tube also permits positioning of the tip of the extension tube adjacent the suture insertion site. According to another embodiment of the present invention, a threading assembly is provided in connection with suture securement assembly. The threading assembly allows a practitioner to quickly and simply thread one or more tails of suture from the exterior of suture securement apparatus and through a lumen of the suture securement apparatus such that desired engagement of such sutures is effectuated.

According to one embodiment of the present invention, a clasp and suture loop are provided as part of the threading assembly. The clasp prevents the accidental pulling of the suture loop through the suture securement apparatus as a result of the tension exerted on the portion of the suture loop positioned distal to the suture securement apparatus. Additionally, the clasp provides a simple and ergonomical mechanism to allow a user to control functioning of threading assembly and of the suture securement loop.

FIG. 1 is a perspective view of a suture securement apparatus according to one embodiment of the present invention. Suture securement apparatus 10 is utilized to selectively and releasably secure the ends of the suture provided in connection with various different types of securement procedures. In the illustrated embodiment, the sutures are utilized with a purse string suture to maintain hemostasis and close a percutaneous catheter puncture site. Suture securement apparatus 10 comprises a body 12, an extension tube 14, release button 16, and an assembly window 18. Body 12 comprises a housing for securing the other components of suture securement apparatus 10 and for maintaining desired operability of the components of suture securement apparatus 10. An extension tube 14 extends distally from body 12. Extension tube 14 provides a mechanism for engaging the sutures positioned adjacent the wound without interruption or interference from body 12 of suture securement apparatus 10. In other words, the length of extension tube 14 allows the tip to be positioned adjacent the suture insertion site to maintain a desired degree of tension on the sutures without interruption from body 12 of suture securement apparatus 10.

Release button 16 is positioned within body 12 of suture securement apparatus 10. Release button 16 allows a practitioner to selectively secure or release sutures positioned within suture securement apparatus 10. For example, in the illustrated embodiment when release button 16 is in a released position, suture securement apparatus is securely gripping any sutures positioned within suture securement apparatus 10. When the user depresses release button 16, the grip exerted by suture securement apparatus 10 on any sutures positioned within suture securement apparatus 10 is loosened, and manipulation of the sutures or adjustment of the suture securement apparatus 10 relative to the sutures can be effectuated. The ability to selectively release and reposition the suture securement apparatus 10 relative to sutures for which the suture securement apparatus 10 is to be utilized can be desirable to the extent the practitioner desires to adjust the tension, reposition the suture securement apparatus 10 relative to the patient, or perform other desired activities relative to the sutures and/or the suture securement apparatus 10.

Assembly window 18 comprises an aperture in the sidewall of body 12 of suture securement apparatus 10. Assembly window 18 allows for the quick snap fit assembly of release button 16 relative to body 12 of suture securement apparatus 10. In the illustrated embodiment, release button 16 includes a biasing flange having a transverse length approximating the width of assembly window 18. During assembly, release button 16 is lowered into body 12 of suture securement apparatus 10. As release button 16 is urged downward, the biasing flange is received within assembly window 18 preventing inadvertent removal of release button 16 from body 12.

In the illustrated embodiment, suture securement apparatus 10 is utilized with threading assembly 20. Threading assembly 20 allows a practitioner to quickly and simply thread one or more tails of suture 32 from the exterior of suture securement apparatus 10 and through a lumen of the suture securement apparatus 10 such that desired engagement of such sutures is effectuated. In the illustrated embodiment, threading assembly 20 comprises a suture loop 22 and a clasp 24. Suture loop 22 extends from a proximal portion of suture securement apparatus 10, along the length of a lumen of suture securement apparatus, and extends distally from an end of extension tube 14.

In the illustrated embodiment, clasp 24 includes a first lateral side and second lateral side. Cooperative engagement of the first lateral side and second lateral side secures a portion of suture loop 22 within clasp 24. Clasp 24 secures the end of suture loop 22 positioned on the proximal side of suture securement apparatus 10. Clasp 24 prevents the accidental pulling of suture loop 22 through suture securement apparatus 10 as a result of tension exerted on the portion of suture loop 22 positioned distal to suture securement apparatus 10. Additionally, clasp 24 provides a simple and ergonomical mechanism to allow a user to control functioning of threading assembly and of suture securement loop 22. According to one embodiment of the present invention, clasp 24 includes texturing or finger grips to allow for desired gripping of clasp 24.

In the illustrated embodiment, a suture 32 is utilized in connection with a puncture site 30. As will be appreciated by those skilled in the art, a variety of types and configurations of puncture sites can be utilized with sutures. For example, a percutaneous catheter puncture site can result in a round or substantially circular wound similar to that depicted as puncture site 30. Suture 32 is configured as a purse string suture. As a result, a plurality of purse string segments 34a, b, c are depicted being positioned around the perimeter of puncture site 30. A first tail is shown extending away from puncture 30. A second tail 38 is also depicted as extending away from puncture site 30. First tail 36 and second tail 38 are positioned adjacent to one another but in sufficient spatial relationship so as to allow the drawing of first tail 36 closer to second tail 38 to achieve a desired degree of tension on purse string segments 34a, b, c. In the illustrated embodiment, a user can utilize suture securement apparatus 10 to achieve a desired degree of tension on the purse string configuration of suture 32.

To utilize suture securement apparatus 10, a user simply threads the first tail 36 and second tail 38 through suture loop 22. Once the first tail 36 and second tail 38 are threaded through suture loop 22, the user grasps clasp 24 and begins to draw suture loop 22 in a proximal direction. As suture loop 22 is retracted in a proximal direction it begins to be drawn into extension tube 14. As suture loop 22 is drawn into extension tube, first tail 36 and second tail 38 are also drawn into extension tube 14. In this manner, complicated or cumbersome introduction of the tips of first tail 36 and second tail 38 into the somewhat small diameter of extension tube 14 is unnecessary. A more complete description of the manner in which suture loop 22 is utilized to draw first tail 36 and second tail 38 of the suture 32 into suture securement apparatus 10 will be described with reference to FIG. 2.

As will be appreciate by those skilled in the art, a variety of types and configurations of suture securement apparatus and threading assembly can be utilized without departing from the scope and spirit of the present invention. According to one embodiment of the present invention, the suture securement apparatus and threading assembly are provided as a unified component. According to another embodiment of the present invention, the suture securement apparatus and threading assembly are separate components that can be utilized alone or in combination. According to another embodiment of the present invention, the suture securement apparatus can be utilized with a suture configuration other than a purse string suture.

Figure 2:
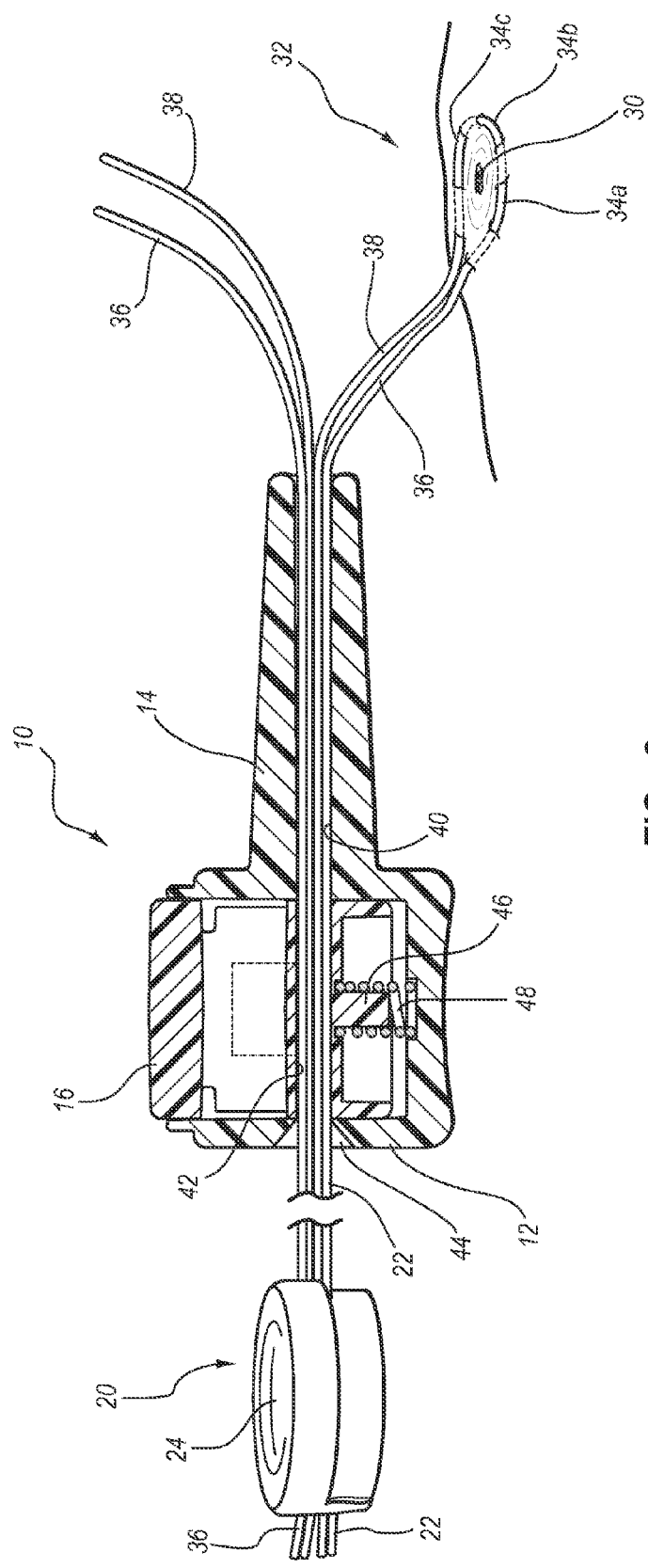
FIG. 2 is a cross-sectional side view of the suture securement apparatus illustrating operation of the threading assembly for threading sutures through the suture securement apparatus according to one aspect of the present invention.

FIG. 2 is a cross-sectional side view of suture securement apparatus 10 according to one embodiment of the present invention. In the illustrated embodiment, suture securement apparatus 10 illustrates the use of threading assembly 20 to draw the first tail 36 and second tail 38 through suture securement apparatus 10. In the illustrated embodiment, a practitioner has grasped clasp 24 and is pulling clasp 24 in a rearward direction. First tail 36 and second tail 38 have been threaded through suture loop 22. As a result, when clasp 24 is retracted in a rearward direction, suture loop 22 is drawn into an extension tube lumen 40 of extension tube 14. Because first tail 36 and second tail 38 are threaded through suture loop 22, retraction of suture loop 22 pulls first tail 36 and second tail 38 into extension tube lumen 40.

As the practitioner continues to pull clasp 24 and suture loop 22 in a rearward direction, the end of suture loop 22 is drawn into a release button lumen 42. As a result, first tail 36 and second tail 38 are drawn into release button lumen 42. As will be appreciated by those skilled in the art, as the practitioner continues to retract threading assembly 20 in a rearward direction, the first tail 36 and second tail 38 are pulled along the entire length of suture securement apparatus until first tail 36 and second tail 38 extend out of a rear aperture 44 and from a proximal portion of suture securement apparatus 10. In this manner, threading assembly 20 facilitates the simple and quick threading of the first tail 36 and second tail 38 of suture 32 through suture securement apparatus 10.

In the illustrated embodiment, release button 16 includes a post 46 and a spring member 48. Spring member 48 is positioned adjacent post 46 such that spring member 48 exerts a biasing force urging release button 16 in an upward direction. When spring member 48 has urged post 46 in an upward direction such that release button 16 is at its upward most displacement relative to body 12, release button lumen 42 is placed slightly out of alignment with extension tube lumen 40. In this manner, first tail 36 and second tail 38 of suture 32 are sandwiched between the bottom surface of release button lumen 42 and the top surface of extension tube lumen 40. Similarly, first tail 36 and second tail 38 of suture 32 are sandwiched between the bottom surface of release button lumen 42 and the top surface of rear aperture 44. The cooperative engagement of the surfaces of extension tube lumen 40, release button 42, and rear aperture 44 provide an effective mechanism for securing a desired degree of tension on first and second tails 36 and 38 of suture 32 positioned along the length of suture securement apparatus 10.

When a practitioner desires to loosen the tension on first tail 36 and second tail 38 of suture 32, the practitioner simply depresses release button 16. As the practitioner depresses release button 16, the release button 16 is urged in a downward direction. As the release button 16 is urged in a downward direction, spring member 48 is depressed. Additionally, as the release button 16 is urged in a downward direction, the release button lumen 42 becomes aligned with extension tube lumen 40 and rear aperture 44. As a result, first tail 36 and second tail 38 of suture 32 are no longer cooperatively engaged between opposing surfaces of release button lumen 42, extension lumen 40, and rear aperture 44. This allows the practitioner to move suture securement apparatus laterally relative to first tail 36 and second tail 38. Releasing of this securement of suture 32 by depression of release button 16 allows the practitioner to loosen, tighten, or make other changes in the juxtaposition of suture securement apparatus 10 relative to suture 32.

In the illustrated embodiment, rear aperture 44 is positioned in substantial alignment with extension tube lumen 40. Additionally, rear aperture 44 has a tapered configuration which facilitates the loading of suture loop 22 along the length of suture securement apparatus 10. According to one embodiment of the present invention, a tapered extension tube is provided in place of rear aperture 44.

As will be appreciated by those skilled in the art, a variety of types and configurations of suture securement apparatus can be utilized without departing from the scope and spirit invention. For example, in one embodiment, the extension tube has a tapered distal aperture to facilitate loading of sutures into the suture securement apparatus. According to another embodiment of the present invention, the suture securement apparatus is provided without a threading assembly. According to yet another embodiment of the present invention, the juxtaposition and mechanism utilized to secure a suture relative to the suture securement apparatus other than a release button is utilized.

Figure 3:
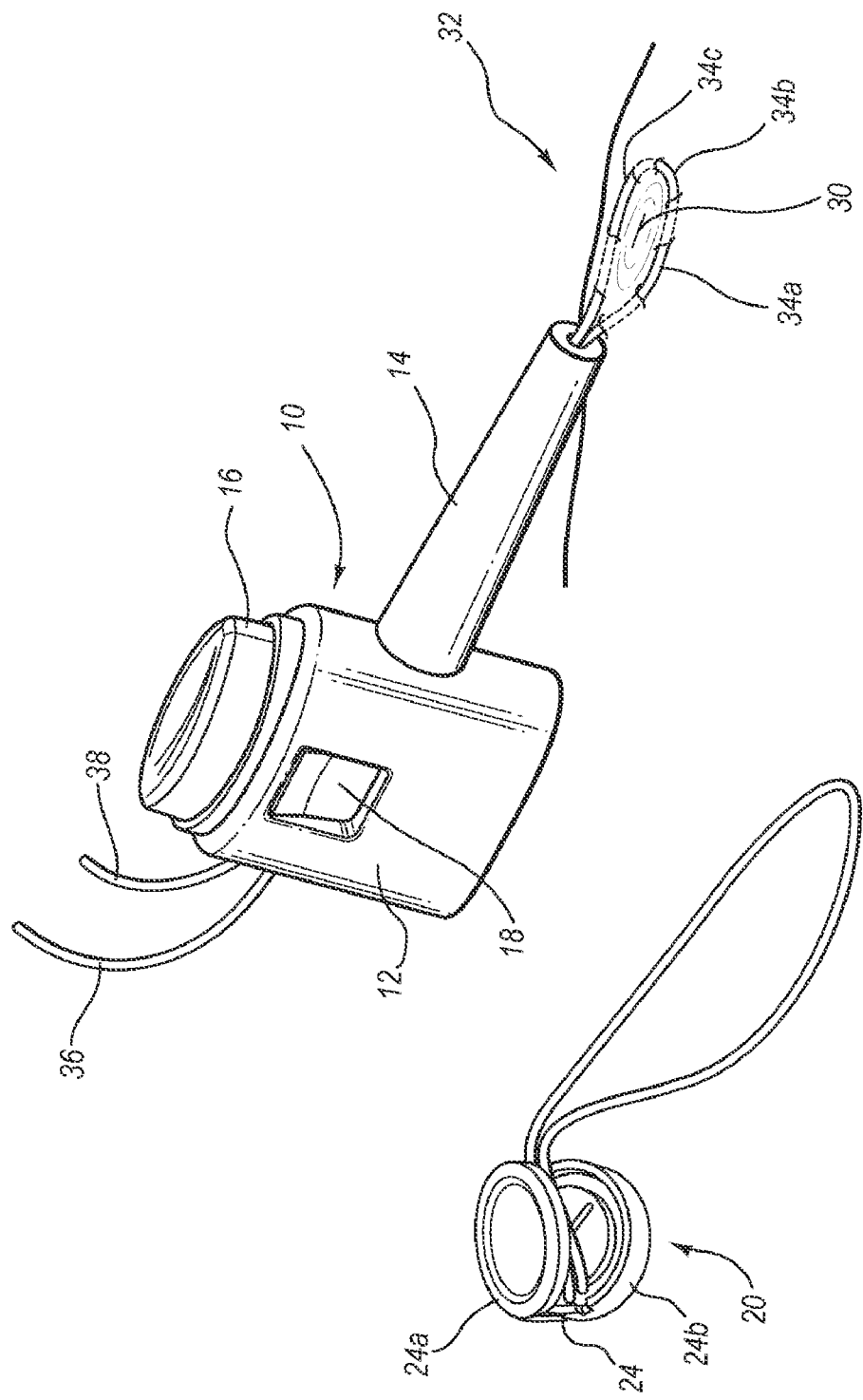
FIG. 3 is a perspective view of the suture securement apparatus illustrating the manner in which the suture securement apparatus maintains a desired degree of tension on the purse string sutures at a puncture wound site.

FIG. 3 is a perspective view of a suture securement apparatus 10 according to one embodiment of the present invention. In the illustrated embodiment, first tail 36, and second tail 38 have been threaded along the entire length of suture securement apparatus 10 such that first tail 36 and second tail 38 are extending out through rear aperture 44 (see FIG. 2). Suture securement apparatus 10 has been advanced forward such that the tip of extension tube 14 is positioned adjacent the insertion sites of first tail 36 and second tail 38 into the patient. In other words, first tail 36 and second tail 38 have been pulled tight relative to suture securement apparatus 10 such that a desire degree of tension is exerted on the purse string suture segments 34a, b, c. As a result, puncture site 30 is effectively closed and hemostasis at the puncture site 30 is effectuated.

In the illustrated environment, suture loop 22 has been fully withdrawn form suture securement apparatus 10. Additionally, clasp 24 is shown in an open configuration to illustrate the mechanism by which clasp 24 secures the configuration of suture loop 22. In the illustrated embodiment, clasp 24 has a clam shell configuration. Clasp 24 comprises a first clam shell component 24A and a second clam shell component 24a. The underlying surfaces of clam shell 24a and clam shell 24b have a profile which facilitates closing and gripping of the suture from which suture loop 22 is formed. Additionally, when the clam shell 24a and clam shell 24b are pressed together, a snap fit or other engagement mechanism is effectuated which secures the closed configuration of clasp 24.

Figure 4:
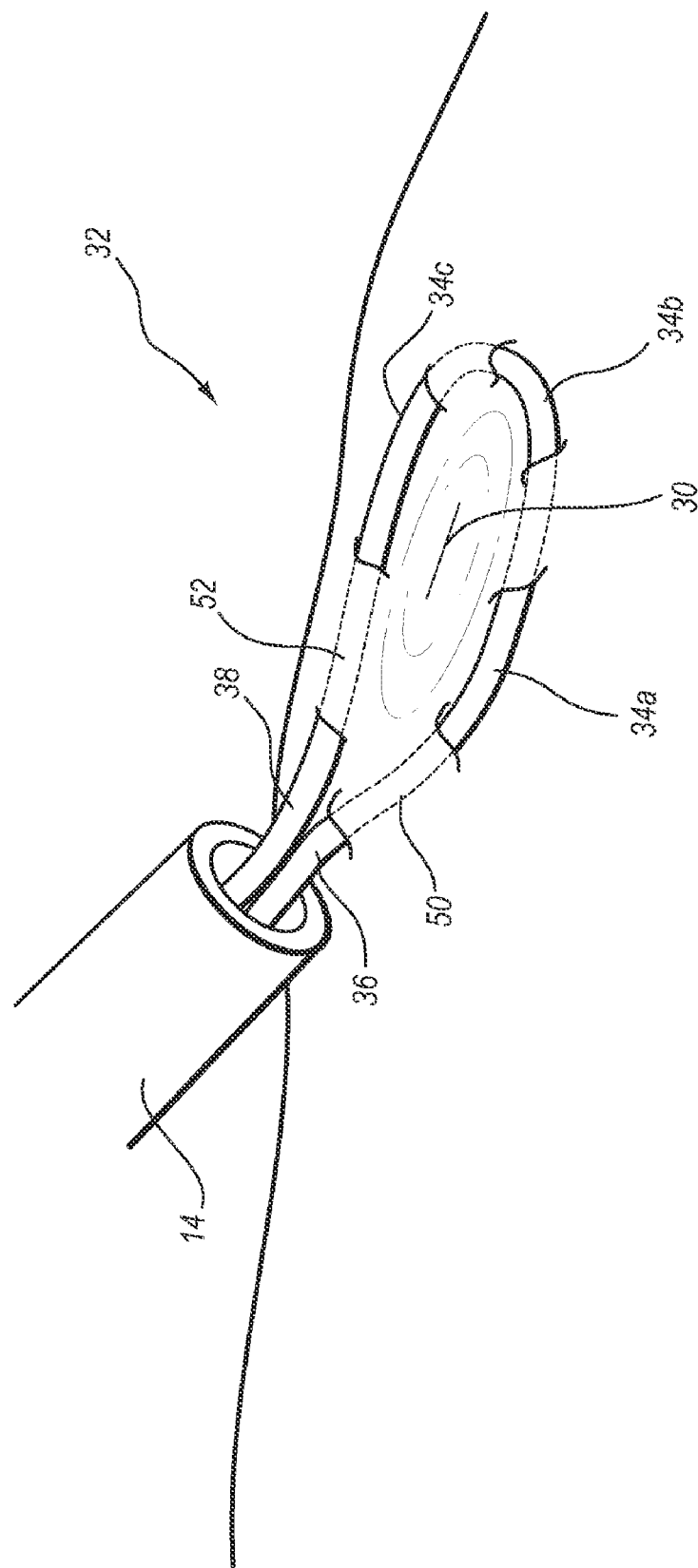
FIG. 4 is a close-up perspective view of an extension tube illustrating the juxtaposition of the extension tube relative to the tails of the suture at a puncture wound site.

FIG. 4 is a close up perspective view of the tip of extension tube 14 relative to the purse string suture configuration positioned around puncture site 30. In the illustrated embodiment, first tail 36 and second tail 38 are threaded into extension tube lumen 40. It can be seen that the diameter of extension tube lumen 40 at the tip of extension tube 14 is smaller than the distance between the primary suture insertion point 50 at which first tail 36 is inserted into the patient and the secondary suture emergence point 52 at which second tail emerges from the patient. By having a diameter of extension tube lumen 40 that is smaller than the distance between primary suture insertion point 50 and secondary suture emergence point 52, tension exerted on first tail 36 and second tail 38 draws first tail 36 and second tail 38 together at the extension tube lumen 40. By drawing the first tail 36 and second tail 38 together, desired tensioning of the entire purse string suture along the perimeter of puncture site 30 is effectuated. This helps to minimize puckering or other distortion of the skin surrounding puncture site 30. As a result, desired closure of the puncture site 30 is effectuated and inadvertent damage for improper healing of the puncture site 30 is avoided.

As will be appreciative of those skilled in the art, a variety of types and configurations and methods of securing a suture relative to the suture securement apparatus 10 can be utilized without departing from the scope and spirit of the present invention. For example, in one embodiment, only the very tip of the extension tube lumen 40 has a smaller diameter than the distance between the primary suture insertion point 50 and the secondary suture emergence point 52. According to another embodiment of the present invention, the entire length of the extension tube lumen 40 has a smaller diameter than the distance between the primary suture insertion point 50 and the secondary suture emergence point 52. According to yet another embodiment of the present invention, a method of tying or wrapping the first and second tails of the suture can be utilized without departing from the scope and spirit of the present invention. According to yet another embodiment of the present invention, the suture securement apparatus 10 is utilized with a suture arrangement other than a purse string suture.

As will be understood by those skilled in the art, utilization of the suture securement apparatus with the purse string suture is merely an exemplary embodiment illustrating operation of the suture securement apparatus relative to sutures and should in no means be considered to be limiting in nature. For example, the suture securement apparatus can be utilized with sutures that are not affixed to the skin of the patient. Additionally, the suture securement apparatus can be utilized for securing additional medical devices such as a suture ring of a catheter hub to a patient. According to another embodiment, the suture securement apparatus is utilized with sutures which are not utilized at a catheter insertion point.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suture securement apparatus for selectively and releasably securing the ends of a suture utilized in a purse string suture utilized to maintain hemostasis and close a percutaneous catheter puncture site, the suture securement apparatus comprising:
   a body having a cavity positioned therein; a suture having a first end, a second end, a loop portion, a first portion extending between the first end and the loop portion, and a second portion extending between the second end and the loop portion;
   a plunger slidably disposed within the cavity of the body, the plunger being slidable between a first position in which the ends of the suture are secured relative to the suture securement apparatus and a second position in which the ends of the suture can be moved relative to the suture securement apparatus, the plunger defining a plunger lumen that extends through the plunger, the plunger lumen having a bottom surface, and is configured to receive the first and second portions of the suture;
   a biasing spring positioned within the cavity of the body and engaging the plunger to bias the plunger toward the first position and allow for releasable engagement of the sutures;
   an extension tube extending a predetermined distance from the body such that a tip of the extension tube is configured to engage the first and second portions of the suture adjacent a suture insertion point without interruption from the body, the extension tube defining an extension tube lumen that extends through the extension tube, has a top surface, and is configured to receive the first and second portions of the suture; and a threading assembly having a base portion and a suture engaging portion for facilitating of the suture through a lumen of the suture securement apparatus, the threading assembly selectively coupleable to the first and second portions of the suture; wherein the suture is configured to be disposed within the plunger lumen and the extension tube lumen such that the loop portion extends from the extension tube lumen and the first and second ends extend from the body, the threading assembly configured to be coupled to the first and second portions of the suture,
   wherein when the plunger is in the first position the plunger lumen and the extension tube lumen are misaligned such that the suture ends are secured by engagement first and second portions of the suture of the between the bottom surface of the plunger lumen and the top surface of the extension tube lumen.

2. The suture securement apparatus of claim 1, wherein the plunger comprises a release button.

3. The suture securement apparatus of claim 1, wherein the tip of the extension tube is configured to have a smaller outside diameter than a distance between a primary suture insertion point at which a first suture end is inserted into a patient and a secondary suture emergence point at which a second suture end emerges from the patient, such that tension exerted on the suture ends from position proximal to and in a direction proximal to the suture securement apparatus draws the suture ends together at the tip of the extension tube.

4. The suture securement apparatus of claim 3, wherein the plunger includes a post and the biasing member is positioned adjacent the post such that the biasing member urges the post in an upward direction.

5. The suture securement apparatus of claim 4, wherein the first and second portions of the suture secured by the suture securement apparatus can be moved relative to the suture securement apparatus when the extension tube lumen and the plunger lumen are aligned.

6. The suture securement apparatus of claim 4, wherein sutures secured by the suture securement apparatus are secured relative to the suture securement apparatus when the extension tube lumen and the plunger lumen are not aligned.

7. The suture securement apparatus of claim 1, wherein the extension tube is integrally coupled to the body of the suture securement apparatus.

8. The suture securement apparatus of claim 1, wherein the tip of the extension tube has a smaller outside diameter than the outside diameter of the portion of the extension tube positioned adjacent the body.

9. The suture securement apparatus of claim 1, further comprising a window in a sidewall of the body, the window configured to receive a biasing flange of the plunger to enable a snap fit assembly that secures the plunger into the cavity of the body such that the plunger is slidably disposed in the cavity.

* * * * *